United States Patent
Kim et al.

(10) Patent No.: US 10,589,119 B2
(45) Date of Patent: Mar. 17, 2020

(54) SMARTPHONE INTERFACE DEVICE FOR PHOTOTHERAPY

(71) Applicants: Color Seven Co., Ltd., Seoul (KR); Nam Gyun Kim, Seoul (KR); Kyoung Jun Park, Seoul (KR)

(72) Inventors: Nam Gyun Kim, Seoul (KR); Kyoung Jun Park, Seoul (KR)

(73) Assignees: COLOR SEVEN CO., LTD., Seoul (KR); Nam Gyun Kim, Seoul (KR); Kyoung Jun Park, Seoul (KR)

( * ) Notice: Subject to any disclaimer, the term of this patent is extended or adjusted under 35 U.S.C. 154(b) by 101 days.

(21) Appl. No.: 15/522,109

(22) PCT Filed: Nov. 9, 2015

(86) PCT No.: PCT/KR2015/011975
§ 371 (c)(1),
(2) Date: Apr. 26, 2017

(87) PCT Pub. No.: WO2016/072812
PCT Pub. Date: May 12, 2016

(65) Prior Publication Data
US 2017/0333727 A1  Nov. 23, 2017

(30) Foreign Application Priority Data

Nov. 7, 2014 (KR) .................. 10-2014-0154254
Nov. 6, 2015 (KR) .................. 10-2015-0155884

(51) Int. Cl.
*A61N 5/06* (2006.01)
*H04M 1/725* (2006.01)
(Continued)

(52) U.S. Cl.
CPC .......... *A61N 5/06* (2013.01); *H04M 1/72527* (2013.01); *H04M 19/04* (2013.01); *A61N 5/0618* (2013.01);
(Continued)

(58) Field of Classification Search
CPC ...... A61N 5/06; A61N 5/0613; A61N 5/0616; A61N 5/0618; A61N 5/0619; A61N 5/062;
(Continued)

(56) References Cited

U.S. PATENT DOCUMENTS 7,993,381 B2 * 8/2011 Mac .................... A61N 5/0619
128/907
9,913,993 B2 * 3/2018 Gross .................. A61N 5/0616
(Continued)

FOREIGN PATENT DOCUMENTS

JP      2008-522325 A    6/2008
KR   10-2012-0131316 A  12/2012
(Continued)

*Primary Examiner* — Ahmed M Farah
(74) *Attorney, Agent, or Firm* — Rabin & Berdo, P.C.

(57) ABSTRACT

The present invention relates to a smartphone interface device for phototherapy which performs communication with a smartphone by using a micro controller unit (MCU) installed in the smartphone interface device for phototherapy and a universal serial bus on-the-go (USB OTG) module, and is capable of controlling a light beam irradiator more stably to enable the light beam irradiator to be driven. The present invention pertains to a smartphone interface device for phototherapy comprising: a micro controller unit (MCU) for receiving, from a smartphone, light beam irradiation intensity, light beam irradiation time, light beam irradiation pattern, and light beam irradiation start and end-relevant light beam irradiating electrode control commands, and generating a light source drive control signal according to the received light beam irradiating electrode control com-
(Continued)

mands; a universal serial bus on-the-go (USB OTG) module; a voltage regulator; and a light beam irradiation drive unit.

13 Claims, 10 Drawing Sheets

(51) Int. Cl.
  *H04M 19/04* (2006.01)
  *H04M 1/21* (2006.01)
(52) U.S. Cl.
  CPC .... *A61N 5/0622* (2013.01); *A61N 2005/0626* (2013.01); *A61N 2005/0644* (2013.01); *H04M 1/21* (2013.01)
(58) Field of Classification Search
  CPC ............... A61N 5/0622; A61N 5/0624; A61N 2005/0626; A61N 2005/063; A61N 2005/0632; A61N 2005/0635; A61N 2005/0643; A61N 2005/0644; A61N 2005/0645; A61N 2005/0651; A61N 2005/0653; H04M 1/725; H04M 1/72519; H04M 1/72527; H04M 1/72563; H04M 1/7258; H04M 1/72583; H04M 1/72586; H04M 1/38; H04M 1/385
  USPC ................................ 607/88–91, 93; 128/898
  See application file for complete search history.

(56) References Cited

U.S. PATENT DOCUMENTS

| | | | |
|---|---|---|---|
| 9,950,188 B2* | 4/2018 | Kim | ..................... A61N 5/0613 |
| 2006/0095642 A1 | 5/2006 | Hesse et al. | |
| 2014/0088668 A1* | 3/2014 | Kim | ......................... A61N 5/06 607/90 |
| 2015/0231402 A1* | 8/2015 | Aghassian | .......... A61N 1/37229 607/59 |
| 2016/0123802 A1* | 5/2016 | Likovich | ................ G01J 1/0271 356/221 |
| 2016/0129281 A1* | 5/2016 | Kim | ..................... A61N 5/0619 607/89 |
| 2017/0105265 A1* | 4/2017 | Sadwick | ............... A61N 5/0618 |
| 2017/0189712 A1* | 7/2017 | Lippert | ................ A61N 5/0601 |
| 2017/0361093 A1* | 12/2017 | Yoo | ......................... A61N 2/006 |
| 2018/0110960 A1* | 4/2018 | Youngblood | ......... A61B 5/0031 |
| 2018/0154167 A1* | 6/2018 | Kim | ........................ G16H 40/63 |
| 2019/0111255 A1* | 4/2019 | Errico | ................ A61N 1/36014 |

FOREIGN PATENT DOCUMENTS

| | | |
|---|---|---|
| KR | 10-2013-0134022 A | 12/2013 |
| KR | 10-2014-0059035 A | 5/2014 |
| KR | 10-2014-0083679 A | 7/2014 |

* cited by examiner

SMARTPHONE INTERFACE DEVICE FOR PHOTOTHERAPY

TECHNICAL FIELD

The present disclosure relates to a smartphone interface device for phototherapy, and more particularly, to a smartphone interface device for phototherapy which performs communication with a smartphone by using a microcontroller unit (MCU) installed in the smartphone interface device for phototherapy and a universal serial bus on-the-go (USB OTG) module for a light beam irradiator to be more stably controlled and driven.

BACKGROUND ART

Phototherapy, in which a human body is stimulated by optical energy from a light beam to treat or prevent a disease, is well-known and is widely used for a purpose of fatigue recovery or skin care or in fields of alternative medicine and pain treatment, etc.

For a phototherapy device to be easily used anytime and anywhere, the present applicant has been developing a light been irradiation treatment device which is connected to a smartphone to drive a light beam irradiator by using power of the smartphone.

Particularly, nowadays, the prediction that smartphones will serve as substitutes for medical devices are being continuously made, and studies for enabling people to directly manage their health using smartphones and precise sensors are coming to the fore. A medical device connected to a smartphone or a tablet personal computer (PC) is able to share data, which is measured to make a patient interested in health management, online with a doctor in real time.

Apple has already been promoting iPhone as a medical device platform for a long time, and nowadays, the entire medical market is focusing on developing a device for this. Particularly, "iStethoscope" which checks heartbeats by using an iPhone's built-in microphone is present, and Withings, which is a France-based venture capital firm, has developed a blood pressure measurement device which is used by being connected to an iPad or an iPhone. The blood pressure measurement device records an automatically measured heart rate and blood pressure in a smartphone. AgaMatrix has collaborated with Sanofi, which is a pharmaceutical firm, and has succeeded in combining "iBGStar," which is a device for measuring glucose in blood, with an iPhone.

The need for performing phototherapy easily and conveniently anytime and anywhere using a smartphone is also being increased in the field of phototherapy devices. However, it is difficult to control a light beam irradiator by connecting the light beam irradiator to a smartphone and simply using an application program.

For example, although an output signal of a smartphone can be used as a power driving signal of a light beam irradiator when the light beam irradiator is connected to a charging port of the smartphone, it is difficult for the signal to be turned on/off or a predetermined control signal to be output.

Also, when a light beam irradiator is connected to an audio output port of a smartphone, because a signal is too weak for the light beam irradiator to be controlled by an audio signal output from the audio output port according to an application program, the light beam irradiator is not properly driven.

A smartphone interface device for phototherapy for enabling a light beam irradiator to be properly driven stably according to an application program by connecting the light beam irradiator to a smartphone and using power of the smartphone is required.

As the related art, Korean Patent Registration No. 10-1385707 "Color therapy system using visible light" is present. In Korean Patent Registration No. 10-1385707, according to a color therapy device operation request signal selected by a user, a color therapy device, which is attached to a color therapy site of a body by a double-sided adhesive tape, a hydrogel pad, an air absorption plate, or the like to be used to intensively irradiate the color therapy site with visible light and has a light source (e.g., a light emitting diode (LED)) embedded therein to emit visible light for color therapy of the body (e.g., visible light in a wavelength band of 400 nm to 800 nm), is connected to a portable smart communication device (e.g., a smartphone), in which a color therapy program for controlling a color therapy operation of a color therapy device is installed, to perform color therapy.

In Korean Patent Registration No. 10-1385707, by connecting a light beam irradiator to an interface terminal of a smart communication device such as a charging port, a USB port, or an audio output port and driving the light beam irradiator by an application program installed in the smart communication device, it is actually impossible to provide a driving power of the light beam irradiator by output signals of the interface terminals and simultaneously control the light beam irradiator according to a selected light beam irradiation time, light beam brightness, light beam irradiation pattern and the like.

Particularly, in Korean Patent Registration No. 10-1385707, a disconnecting/connecting gender is used for connecting or disconnecting power jacks of a plurality of color therapy devices to or from a single smart communication device, and has a switch for simultaneously starting or ending the plurality of color therapy devices to start or end the color therapy devices.

However, in Korean Patent Registration No. 10-1385707, the disconnecting/connecting gender is for connecting or disconnecting, and it is actually difficult to control a light beam irradiation time, light beam brightness, and a light beam irradiation pattern of the color therapy device by the disconnecting/connecting gender, and it is difficult for the color therapy device to be stably driven due to being affected by a smartphone.

Consequently, a smartphone interface device for phototherapy having a separate microcontroller unit (MCU) is proposed. By connecting the smartphone interface device for phototherapy, which is connected to a light beam irradiator, to a smartphone via a universal serial bus on-the-go (USB OTG) module, the light beam irradiator can be driven more stably, and a larger variety of light beam irradiators can be driven and controlled.

DISCLOSURE

Technical Problem

It is an aspect of the present disclosure to provide a smartphone interface device for phototherapy which performs communication with a smartphone by using a microcontroller unit (MCU) installed in the smartphone interface device for phototherapy and a universal serial bus on-the-go (USB OTG) module to allow a light beam irradiating electrode to be controlled and driven more stably.

It is another aspect of the present disclosure to provide a smartphone interface device for phototherapy which includes a USB OTG module, a voltage regulator, an MCU, a light beam irradiation driving part, and a light beam irradiating electrode connector to allow a light beam irradiating electrode to be controlled and driven.

It is still another aspect of the present disclosure to provide a smartphone interface device for phototherapy which allows a light beam irradiating electrode to be controlled and driven by a light beam irradiation controlling application program installed and run in a smartphone.

It is yet another aspect of the present disclosure to provide a smartphone interface device for phototherapy which allows a light beam irradiating electrode to be controlled and driven according to a light beam irradiation controlling application program installed and run in a smartphone so as to treat diseases such as arthritis, pain, apoplexy, Alzheimer's disease, angina, edema, rhinitis, migraine, asthma, infertility, a prostate, urinary incontinence, and menstrual pain.

Technical Solution

To achieve the above aspects, the present disclosure provides a smartphone interface device for phototherapy having one side connected to a light beam irradiating electrode and the other side connected to a smartphone to receive a light beam irradiating electrode control command generated by driving an application program installed in the smartphone and control driving of the light beam irradiating electrode. The smartphone interface device for phototherapy includes a microcontroller unit (MCU) configured to receive a light beam irradiating electrode control command related to a light beam irradiation intensity, a light beam irradiation time, a light beam irradiation pattern, and starting and ending of light beam irradiation from the smartphone and generate a light source driving control signal according to the received light beam irradiating electrode control command, a universal serial bus on-the-go (USB OTG) module connected to a smartphone connector and the MCU and configured to perform communication between the smartphone and the MCU with the smartphone as a host, a voltage regulator configured to convert a voltage output from the smartphone into an operating voltage of the MCU, and a light beam irradiation driving part configured to drive a light source according to the light source driving control signal received from the MCU.

The smartphone interface device for phototherapy may further include a light beam irradiating electrode connector configured to connect the light beam irradiating electrode, and an LED operation indicator light configured to indicate that the light beam irradiation driving part is driven and light is radiated from the light source.

A light beam irradiation intensity, a light beam irradiation time, a light beam irradiation pattern, and starting and ending values of light beam irradiation set by a user in an application program installed in the smartphone may be transmitted to the MCU through the USB OTG module.

The present disclosure provides a smartphone interface device for phototherapy having one side connected to a light beam irradiating electrode and the other side connected to a smartphone to receive a light beam irradiating electrode control command generated by driving an application program installed in the smartphone and control driving of the light beam irradiating electrode. The smartphone interface device for phototherapy includes a main body having an MCU, which is configured to receive a light beam irradiating electrode control command related to a light beam irradiation intensity, a light beam irradiation time, a light beam irradiation pattern, and starting and ending of light beam irradiation from the smartphone and generate a light source driving control signal according to the received light beam irradiating electrode control command, embedded therein, a connecting cable connected to one side of the main body and configured to connect a smartphone connector, a light beam irradiating electrode connector connected to the other side of the main body and configured to connect the light beam irradiating electrode, and a USB OTG module embedded in the main body, connected to the smartphone connector and the MCU, and configured to perform communication between the smartphone and the MCU with the smartphone as a host.

The smartphone interface device for phototherapy may further include a voltage regulator embedded in the main body and configured to convert a voltage output from the smartphone into an operating voltage of the MCU, a light beam irradiation driving part embedded in the main body and configured to drive a light source according to the light source driving control signal received from the MCU, and an LED operation indicator light disposed at an upper surface of the main body and configured to indicate that the light beam irradiation driving part is driven and light is radiated from the light source.

The smartphone is one of a smartphone using the Android operating system, a tablet using the Android operating system, a smart watch using the Android operating system, an Apple iPhone, an Apple iPad, and an Apple iWatch.

One of a USB for a smartphone using the Android operating system, a USB for a smart watch using the Android operating system, a USB for an Apple iPhone, and a USB for an Apple iWatch is used as the smartphone connector.

One of an audio terminal and a micro USB is used as the light beam irradiating electrode connector.

The light beam irradiating electrode is a light beam irradiating electrode included in any one of an arthritis treatment device, a pain treatment device, an angina treatment device, a stroke treatment device, an Alzheimer's treatment device, an apoplexy treatment device, a migraine treatment device, an edema treatment device, a gastric ulcer treatment device, a rhinitis treatment device, an asthma treatment device, an infertility treatment device, a urinary incontinence treatment device, a prostate treatment device, a menstrual pain treatment device, and a depression treatment device.

The present disclosure provides a driving method of a smartphone interface device for phototherapy having one side connected to a light beam irradiating electrode and the other side connected to a smartphone and having a microcontroller unit (MCU), which is configured to receive a light beam irradiating electrode control command generated by driving an application program installed in the smartphone and control driving of the light beam irradiating electrode, embedded therein. The driving method includes an initial setting step in which, when a smartphone controlling application program is run in the smartphone, the MCU reads a light beam irradiation time value, a light beam irradiation intensity value, and a light beam irradiation pattern value set by a user through a screen of the smartphone; a driving starting step in which, after the initial setting step, the MCU receives a start button value from the smartphone and, when the received start button value is input as a preset driving starting value, generates a light source driving control signal according to the light beam irradiation time value, the light beam irradiation intensity value, and the light beam irradiation pattern value read in the initial setting step, and transmits the generated light source driving control signal to a light beam irradiation driving part while the MCU simultaneously starts operation of a time counter; and a light irradiation time end determining step in which the MCU determines whether a value of the time counter is equal to or larger than a preset light irradiation time and, when the value of the time counter is equal to or larger than the preset light irradiation time, ends the operation of the light beam irradiation driving part.

The driving method may further include, between the driving starting step and the light irradiation time end determining step, a light irradiation stop determining step in which the MCU receives a stop button value from the smartphone and, when the stop button value is a preset driving stop value, ends the operation of the light beam irradiation driving part.

In the light beam irradiation time end determining step or the light irradiation stop determining step, when the operation of the light beam irradiation driving part is ended, the smartphone may generate an alarm or vibration to inform of the end.

Advantageous Effects

According to the present disclosure, a smartphone interface device for phototherapy performs communication with a smartphone by using a microcontroller unit (MCU) installed in the smartphone interface device for phototherapy and a universal serial bus on-the-go (USB OTG) module, thereby allowing a light beam irradiating electrode to be controlled and driven more stably.

According to the present disclosure, a smartphone interface device for phototherapy includes a USB OTG module, a voltage regulator, an MCU, a light bean irradiation driving part, and a light beam irradiating electrode connector, thereby having a simple configuration and allowing a light beam irradiator to be driven more stably and a larger variety of light beam irradiators to be driven and controlled.

The present disclosure allows a light bean irradiating electrode to be controlled and driven by a light beam irradiation control application program installed and run in a smartphone, thereby allowing phototherapy suitable for one's own disease to be easily and conveniently performed anytime and anywhere using a smartphone. Further, a smartphone interface device for phototherapy according to the present disclosure can be used by being connected to a conventional phototherapy device.

Particularly, the present disclosure allows a light beam irradiating electrode to be controlled and driven according to a light beam irradiation controlling application program installed and run in a smartphone so as to treat diseases such as arthritis, pain, apoplexy, Alzheimer's disease, angina, edema, rhinitis, migraine, asthma, infertility, a prostate, urinary incontinence, and menstrual pain. Consequently, a smartphone interface device for phototherapy of the present disclosure can be used by being connected to various anti-inflammatory and pain relieving treatment devices such as an arthritis treatment device, a pain treatment device, an angina treatment device, a stroke treatment device, an Alzheimer's treatment device, an edema treatment device, a gastric ulcer treatment device, a rhinitis treatment device, a migraine treatment device, an asthma treatment device, an infertility treatment device, a urinary incontinence treatment device, a prostate treatment device, and a menstrual pain treatment device which perform a treatment using light beams.

BEST MODE OF THE INVENTION

According to the present disclosure, a smartphone interface device for phototherapy has one side connected to a light beam irradiating electrode and the other side connected to a smartphone to receive a light beam irradiating electrode control command generated by driving an application program installed in the smartphone and control driving of the light beam irradiating electrode, and includes a universal serial bus on-the-go (USB OTG) module, a voltage regulator, a microcontroller unit (MCU), a light beam irradiation driving part, a light beam irradiating electrode connector, and a light emitting diode (LED) operation indicator light.

The MCU receives a light beam irradiating electrode control command related to a light beam irradiation intensity, a light beam irradiation time, a light beam irradiation pattern, and starting and ending of light beam irradiation from the smartphone and generates a light source driving control signal according to the received light beam irradiating electrode control command, and the light beam irradiation driving part drives a light source according to the light source driving control signal received from the MCU.

Modes of the Invention

Hereinafter, exemplary embodiments of the present disclosure will be described in detail with reference to the accompanying drawings.

Figure 1:
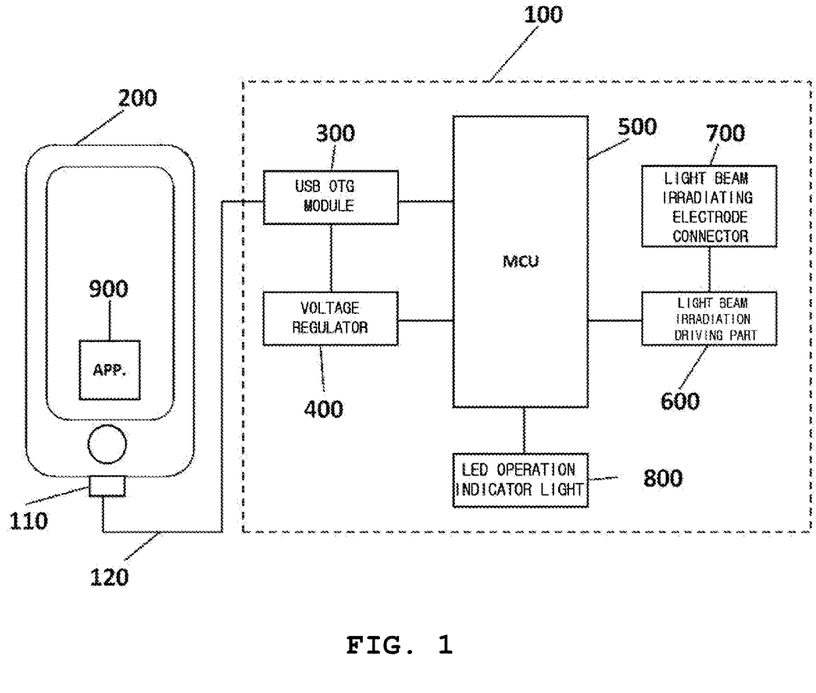
FIG. 1 is a block diagram of a smartphone interface device for phototherapy according to the present disclosure.

FIG. 1 is a block diagram of a smartphone interface device for phototherapy according to the present disclosure which includes a universal serial bus on-the-go (USB OTG) module 300, a voltage regulator 400, a microcontroller unit 500, a light beam irradiation driving part 600, a light beam irradiating electrode connector 700, and a light emitting diode (LED) operation indicator light 800.

The USB OTG module 300 enables communication between a smartphone 200 and the MCU 500 installed in a smartphone interface device for phototherapy 100 with the smartphone 200 as a host.

Generally, to enable point-to-point communication between portable devices such as a smartphone and a personal portable information terminal, the USB OTG module 300 includes a host negotiation protocol (HNP) which enables each of the devices to serve as a host within a limited range and a session request protocol (SRP) which maintains connection only when requested by a partner device so as to reduce power consumption of batteries of the devices.

That is, the USB OTG module 300 connected to the MCU 500 is connected to a smartphone connector 110, and communication between the smartphone 200 and the MCU 500 installed in the smartphone interface device for phototherapy 100 is enabled with the smartphone 200 as a host.

The voltage regulator 400 converts a voltage output from the smartphone 200 into an operating voltage of the MCU 500.

The MCU 500 comprehensively controls the smartphone interface device for phototherapy 100 and controls a light beam irradiation intensity, a light beam irradiation time, a light beam irradiation pattern, a start and an end of light beam irradiation, and the like by interpreting a control command of the smartphone 200 received through the USB OTG module 300. That is, the MCU 500 interprets a control command of the smartphone 200, generates a light source control signal, and transmits the light source control signal to the light beam irradiation driving part 600.

The light beam irradiation driving part 600 drives a light source according to the light source control signal received from the MCU 500. The light beam irradiation driving part 600 includes a voltage or current amplifying circuit required to drive a light source.

The LED operation indicator light 800 is a light configured to display an operation state of light beam irradiation, i.e., is an LED light which indicates that a light beam irradiating electrode is being driven.

The light beam irradiating electrode connector 700 is a connector configured to connect the light beam irradiating electrode, and the smartphone interface device for phototherapy 100 and the light beam irradiating electrode are connected by the light beam irradiating electrode connector 700. Here, various light beam irradiating electrodes may be applied as the light beam irradiating electrode.

An application program (App.) 900 for controlling a light beam irradiation intensity, a light beam irradiation time, a light beam irradiation pattern, and a start and an end of light beam irradiation of the light beam irradiating electrode is installed in the smartphone 200.

In the present disclosure, the smartphone 200 refers to one of a smartphone using the Android operating system, a tablet using the Android operating system, a smart watch using the Android operating system, an Apple iPhone, an Apple iPad, an Apple iWatch, and other mobile devices.

Figure 2A:
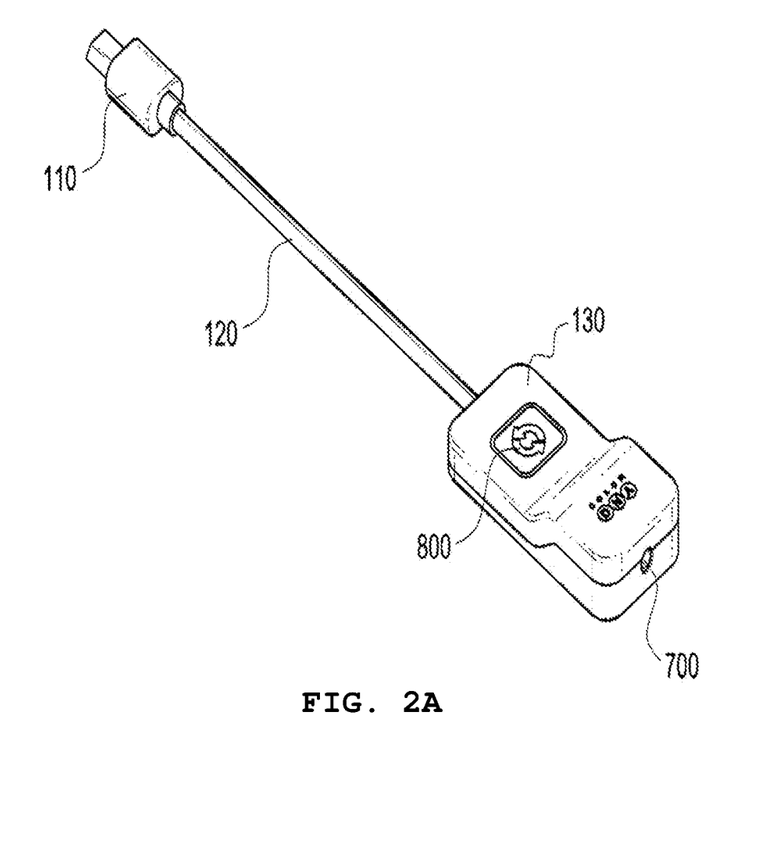
FIG. 2A is a perspective view of a smartphone interface device for phototherapy according to an embodiment of the present disclosure.
Figure 2B:
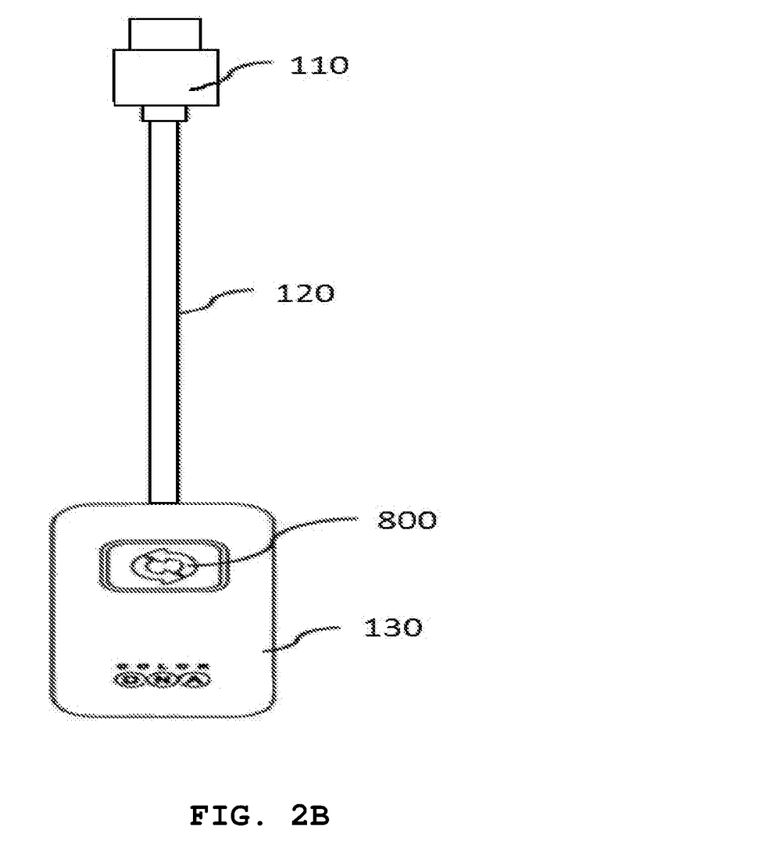
FIG. 2B is a plan view of the smartphone interface device for phototherapy of FIG. 2A.
Figure 2C:
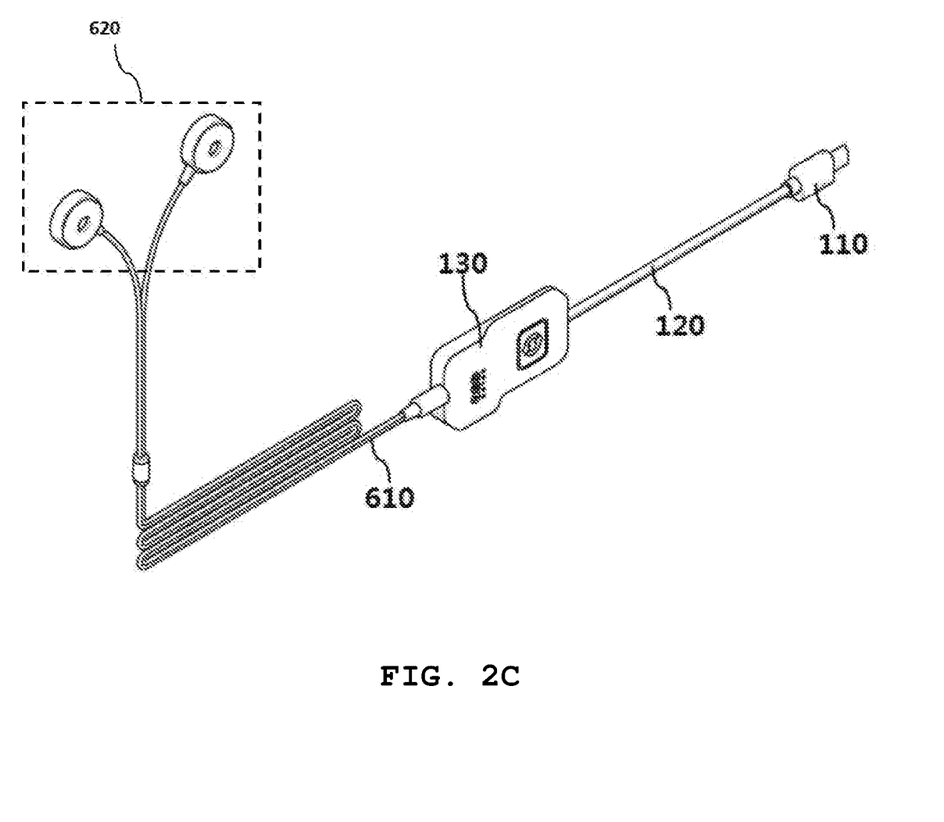
FIG. 2C illustrates a state in which a connecting line connected to a light beam irradiating electrode part is connected to the smartphone interface device for phototherapy of FIG. 2A.

FIG. 2A is a perspective view of the smartphone interface device for phototherapy according to an embodiment of the present disclosure, FIG. 2B is a plan view of the smartphone interface device for phototherapy of FIG. 2A, and FIG. 2C illustrates a state in which a connecting line 610 connected to a light beam irradiating electrode part 620 is connected to the smartphone interface device for phototherapy of FIG. 2A.

The smartphone interface device for phototherapy includes the smartphone connector 110, a connecting cable 120, a main body 130, the LED operation indicator light 800, the light beam irradiating electrode connector 700, etc.

The smartphone connector 110 is connected to the main body 130 via the connecting cable 120. One of a USB for a smartphone using the Android operating system, a USB for a smart watch using the Android operating system, a USB for an Apple iPhone, and a USB for an Apple iWatch may be used as the smartphone connector 110.

The main body 130 has the USB OTG module 300, the voltage regulator 400, the MCU 500, and the light beam irradiation driving part 600 embedded therein, has the light beam irradiating electrode connector 700 disposed at one side thereof, and has the connecting cable 120 disposed at the other side thereof and connected to the smartphone connector 110. The LED operation indicator light 800 and the like is disposed at an upper surface of the main body 130.

One side portion of a housing of the main body 130 is formed to have a larger thickness than the other side portion thereof so that a circuit part including the USB OTG module 300, the voltage regulator 400, and the MCU 500 is disposed in the housing.

The smartphone connector 110 and the light beam irradiating electrode connector 700 may be used by being manufactured as an audio terminal or a micro USB or being manufactured in various ways to be exclusively used for the smartphone interface for phototherapy.

In FIG. 2C, the light beam irradiating electrode part 620 may be a light beam irradiating electrode or a light beam irradiating electrode connector for connecting the light beam irradiating electrode. That is, a light beam irradiating electrode or a light beam irradiating electrode connector is mounted at an end of the connecting line 610.

Figure 3:
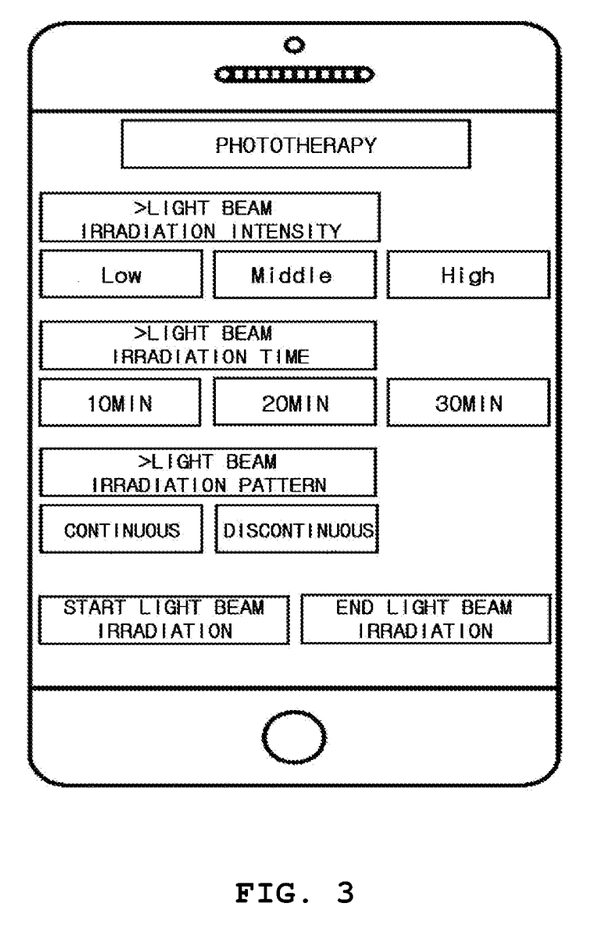
FIG. 3 is an example of a screen of a smartphone in which an application program for controlling the smartphone interface for phototherapy according to the present disclosure is run.

FIG. 3 is an example of a screen of a smartphone in which an application program for controlling the smartphone interface for phototherapy according to the present disclosure is run.

FIG. 3 illustrates that functions for selecting a light irradiation intensity, a light irradiation time, and a light irradiation pattern and functions for selecting a start or an end of light beam irradiation are included in the screen of the smartphone in which the App. 900 for controlling the smartphone interface for phototherapy embedded in the smartphone 200 is run.

Figure 4:
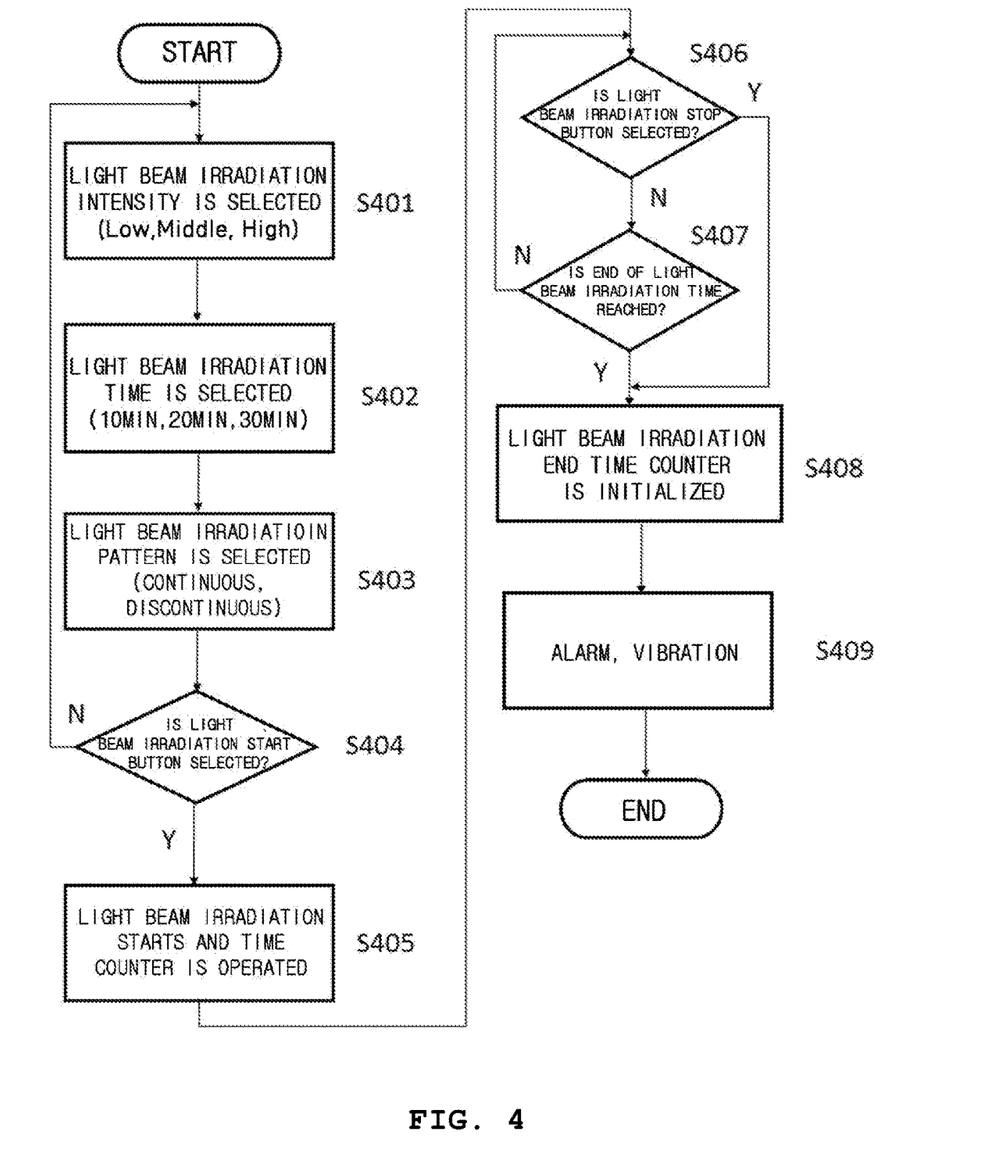
FIG. 4 is a flowchart for describing a method of controlling the smartphone interface for phototherapy according to an embodiment of the present disclosure.

FIG. 4 is a flowchart for describing a method of controlling the smartphone interface for phototherapy according to an embodiment of the present disclosure.

In an initial setting step, when the controlling App. 900 is executed in the smartphone 200, the MCU 500 reads a light beam irradiation time value set by a user (S401), reads a light beam irradiation intensity value set by the user (S402), and reads a light beam irradiation pattern value (S403) from the screen of the smartphone 200.

Here, for example, the light beam irradiation time value may be selected from proposed values such as 10 minutes, 20 minutes, and 30 minutes, or may also be set as any time by the user. Also, the light beam irradiation intensity may also be selected from proposed values such as LOW, MID, and HIGH or may also be freely set by the user by placing a selector at a predetermined position on a bar-shaped line. Also, the light beam irradiation pattern may be selected from two patterns, CONTINUOUS and DISCONTINUOUS, or various pulse forms having discontinuous patterns such as a pulse in which an on-time and an off-time are equal, an on-time is long and an off-time is short, or an on-time is short and an off-time is long may be proposed, and the user may set one of the proposed pulse forms as the light beam irradiation pattern.

In a driving starting step, after the initial setting step, when a start button is selected, i.e., the start button value is input as a preset driving starting value (S404), the MCU 500 generates a light source driving control signal according to the light beam irradiation time value, the light beam irradiation intensity value, and the light beam irradiation pattern value read in the initial setting step and transmits the generated light source driving control signal to the light beam irradiation driving part 600, and the light beam irradiation driving part 600 is driven according to the light source driving control signal and radiates light while the MCU 500 simultaneously starts operation of a time counter (timer) (S405).

In a light irradiation stop determining step, when a light beam irradiation stop button is determined to be selected, i.e., the stop button value is input as a preset driving stop value (S406), the driving method proceeds to an ending step.

In a light irradiation time end determining step, when the light beam irradiation stop button is not selected in the light irradiation stop determining step, whether a value of the time counter (timer) is equal to or larger than a preset light irradiation time is determined. When the value of the time counter (timer) is equal to or larger than the preset light irradiation time, because it signifies that an end of light beam irradiation time is reached, the driving method proceeds to the ending step. When the value of the time counter (timer) is not equal to or larger than the preset light irradiation time, because it signifies that the end of the light beam irradiation time is not reached, the driving method returns to the light irradiation stop determining step (S407). Until the end of the light beam irradiation time is reached, Steps S406 and S407 are repeatedly performed while light irradiation is continued.

In the ending step, light beam irradiation is ended, the time counter is initialized (S408), an alarm or vibration that informs of the end is generated (S409), and the program is ended.

Figure 5:
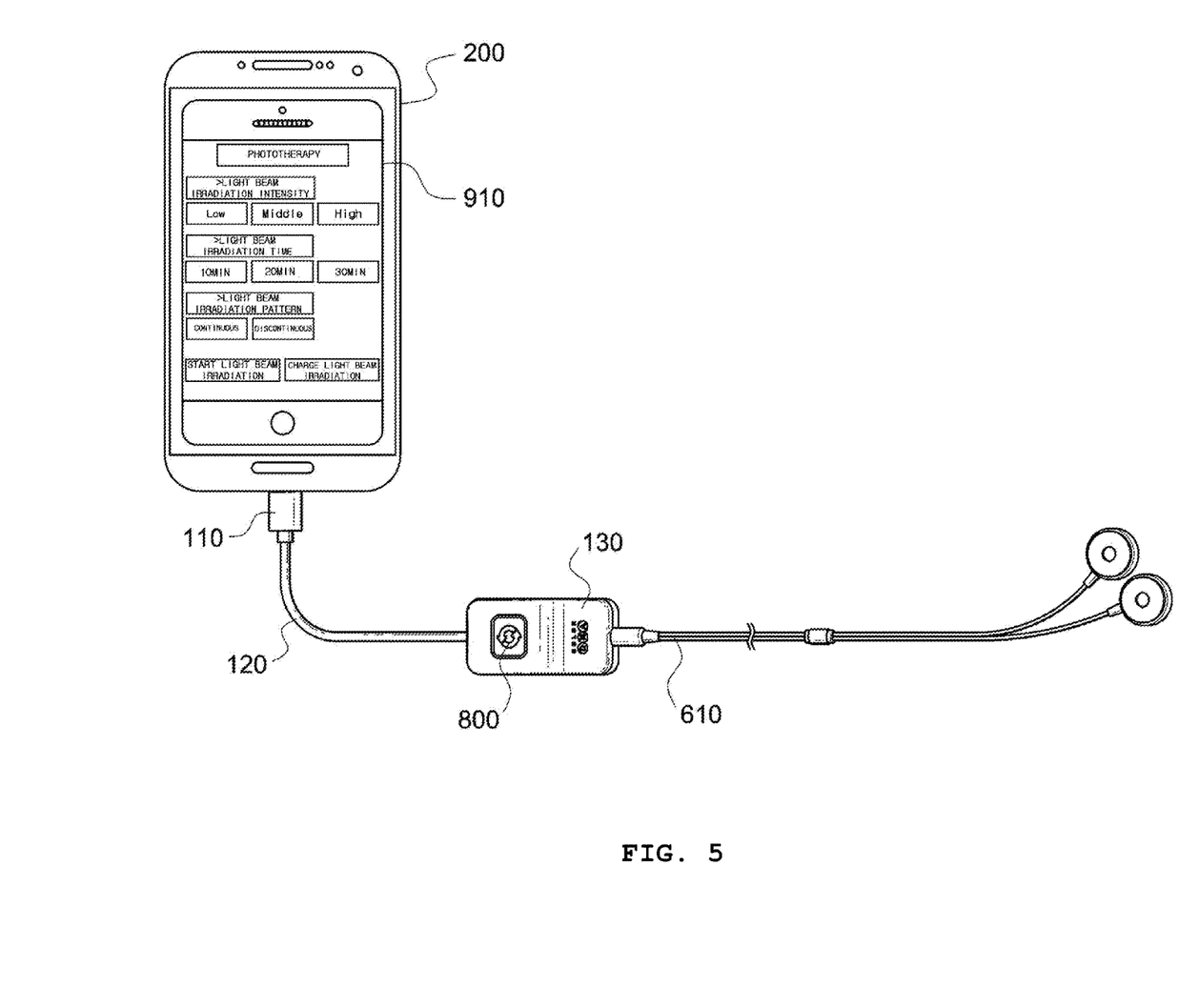
FIG. 5 is a view illustrating an embodiment in which the smartphone interface for phototherapy according to the present disclosure is connected to a smartphone and an electrode for phototherapy.

FIG. 5 is a view illustrating an embodiment in which the smartphone interface for phototherapy according to the present disclosure is connected to a smartphone and an electrode for phototherapy.

The smartphone interface device for phototherapy 100 is connected to the smartphone 200 by using the connector 110, and the connecting line 610 connected to the light beam irradiating electrode part 620 is connected to the light beam irradiating electrode connector 700 so that the user selects a desired light beam irradiation intensity, light beam irradiation time, and light beam irradiation pattern and a light beam irradiation start button from a screen 910 of the smartphone 200 in which the App. 900 for controlling the smartphone interface for phototherapy embedded in the smartphone 200 is run to start light beam irradiation, and the light beam irradiation is automatically ended when an end of the selected light beam irradiation time is reached. Also, to stop light beam irradiation during use, a light beam irradiation end button may be selected to immediately end light beam irradiation.

Figure 6:
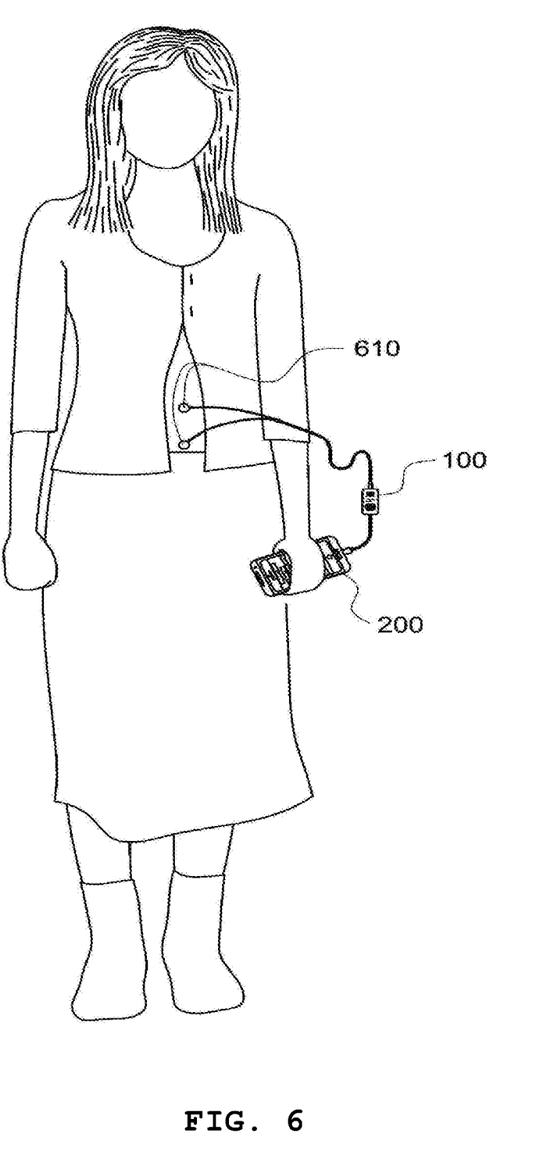
FIG. 6 illustrates an embodiment in which menstrual pain is treated using the smartphone interface for phototherapy according to the present disclosure.

FIG. 6 illustrates an embodiment in which menstrual pain is treated using the smartphone interface for phototherapy according to the present disclosure.

To treat menstrual pain, a user connects the smartphone interface device for phototherapy 100 to the smartphone 200, connects the light beam irradiating electrode part 620 to the smartphone interface device for phototherapy 100, and irradiates a stomach with light beams to treat menstrual pain.

Although not described herein in detail separately using the drawings, the smartphone interface for phototherapy according to the present disclosure is applicable in treating various diseases, which can be treated using only the smartphone and the light beam irradiating electrode, such as arthritis, angina, apoplexy, asthma, the Alzheimer's disease, infertility, migraine, urinary incontinence, a prostate, gastric ulcer, menstrual pain, a carpal tunnel syndrome, and muscular pain. That is, the smartphone interface device for phototherapy according to the present disclosure is applicable to a light beam irradiation device for treating or preventing a disease by irradiating skin with light beams.

For example, the smartphone interface device for phototherapy according to the present disclosure is applicable to an arthritis treatment device for treating arthritis by irradiating a knee joint or joints such as an elbow, a hand, or a foot with light beams, is applicable to an Alzheimer's treatment device for treating the Alzheimer's by irradiating a forehead, a head, a neck, or a face with light beams, is applicable to an apoplexy treatment device for treating apoplexy by irradiating a forehead, a head, a neck, or a face with light beams, is applicable to a migraine treatment device for treating migraine by irradiating a forehead, a head, a neck, a face, a stomach, or a chest with light beams, is applicable to a depression treatment device for treating depression by irradiating a forehead, a head, a neck, a face, a stomach, or a chest with light beams, is applicable to an angina treatment device for treating angina by irradiating a chest or the like with light beams, is applicable to an asthma treatment device for treating asthma by irradiating a neck with light beams, is applicable to a pain treatment device for treating pain by irradiating a shoulder, a neck, a waist, a wrist, an ankle, a calf, or a thigh with light beams, is applicable to a gastritis and gastric ulcer treatment device for treating gastritis and gastric ulcer by irradiating a stomach with light beams, is applicable to a prostate treatment device for treating a prostate by irradiating a lower abdomen or a groin with light beams, is applicable to a urinary incontinence treatment device for treating urinary incontinence by irradiating a lower abdomen or a groin with light beams, is applicable to an infertility treatment device for treating infertility by irradiating a stomach with light beams, and is applicable to a menstrual pain treatment device for treating menstrual pain by irradiating a stomach with light beams.

Figure 7:
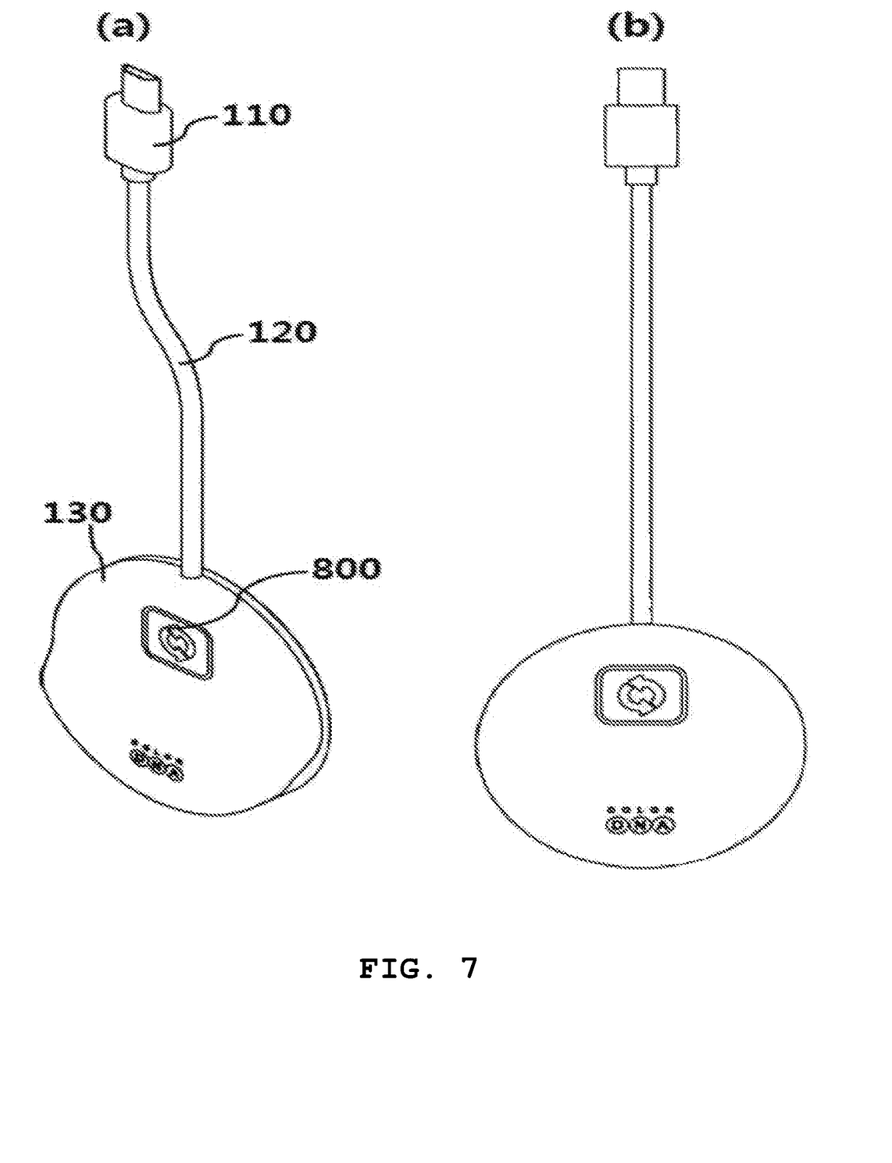
FIG. 7 is a smartphone interface device for phototherapy according to another embodiment of the present disclosure.
Figure 8:
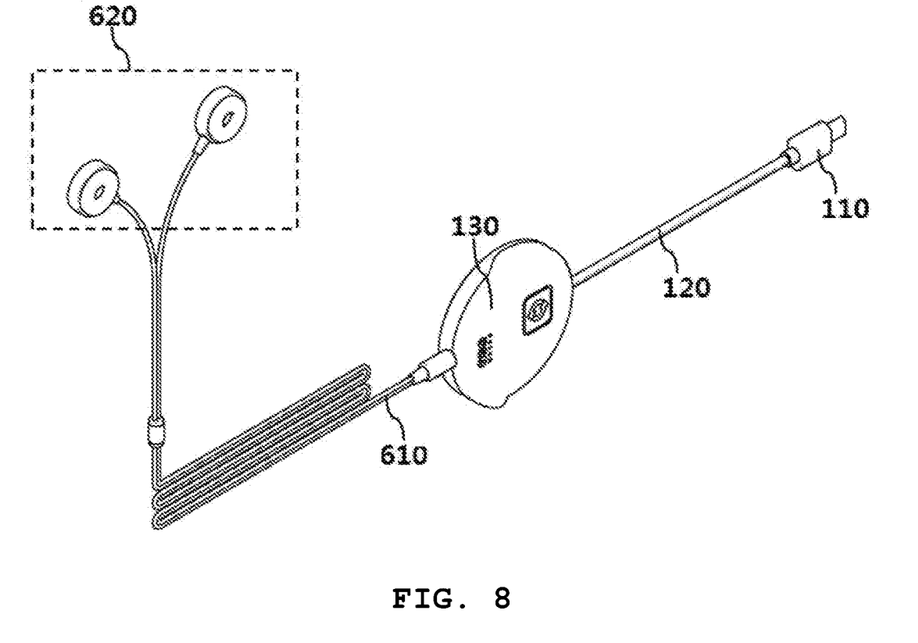
FIG. 8 illustrates a state in which a connecting line (610) connected to a light beam irradiating electrode part (620) is connected to the smartphone interface device for phototherapy of FIG. 7.

FIG. 7 is a smartphone interface device for phototherapy according to another embodiment of the present disclosure, and FIG. 8 illustrates a state in which the connecting line 610 connected to the light beam irradiating electrode part 620 is connected to the smartphone interface device for phototherapy of FIG. 7.

(a) and (b) of FIG. 7 are a perspective view and a plan view of a case in which the main body 130 of the smartphone interface device for phototherapy is formed in a circular shape.

The shape of the smartphone interface device for phototherapy according to the present disclosure is not limited to a quadrilateral shape or a circular shape and may have various shapes such as various polygonal shapes or shapes of various characters.

Particular exemplary embodiments of the present disclosure have been illustrated and described above. However, the present disclosure is not limited to the above-described embodiments, and one of ordinary skill in the art to which the present disclosure pertains should be able to modify and embody the present disclosure in various ways without departing from the gist of the technical spirit of the present disclosure defined in the claims below.

INDUSTRIAL APPLICABILITY

A smartphone interface device for phototherapy according to the present disclosure includes a USB OTG module, a voltage regulator, an MCU, a light beam irradiation driving part, and a light beam irradiating electrode connector, thereby allowing a light beam irradiator to be driven more stably and a larger variety of light beam irradiators to be driven and controlled. In this way, the smartphone interface device for phototherapy can be used for various anti-inflammatory and pain relieving treatments for arthritis, pain, apoplexy, a prostate, urinary incontinence, and menstrual pain.

What is claimed is:

1. A smartphone interface device for phototherapy, the smartphone interface device for phototherapy having one side configured to be connected to a light beam irradiating electrode and another side configured to be connected to a smartphone, the smartphone interface device being further configured to receive a light beam irradiating electrode control command generated by an application program installed in the smartphone, and to control driving of the light beam irradiating electrode, the smartphone interface device for phototherapy further comprising:
    a microcontroller unit (MCU) configured to receive a light beam irradiating electrode control command related to a light beam irradiation intensity, a light beam irradiation time, a light beam irradiation pattern, and starting and ending of light beam irradiation from the smartphone, and to generate a light source driving control signal according to the received light beam irradiating electrode control command;
    a universal serial bus on-the-go (USB OTG) module connected to a smartphone connector and the MCU, and configured to perform communication between the smartphone and the MCU with the smartphone as a host;
    a voltage regulator configured to convert a voltage output from the smartphone into an operating voltage of the MCU; and
    a light beam irradiation driving part configured to receive the light source driving control signal from the MCU and to drive a light source according to the light source driving control signal received from the MCU.

2. The smartphone interface device for phototherapy of claim 1, further comprising:
    a light beam irradiating electrode connector configured to connect the light beam irradiating electrode; and
    an LED (light emitting diode) operation indicator light configured to indicate that the light beam irradiation driving part is driven and light is radiated from the light source.

3. The smartphone interface device for phototherapy of claim 2, wherein one of an audio terminal or a micro USB is the light beam irradiating electrode connector.

4. The smartphone interface device for phototherapy of claim 1, wherein the light beam irradiation intensity, the light beam irradiation time, the light beam irradiation pattern, and the starting and ending values of light beam irradiation are settable by a user in an application program installed in the smartphone, and are transmitted to the MCU through the USB OTG module.

5. The smartphone interface device for phototherapy of claim 1, wherein the smartphone is one of a smartphone configured to use an Android operating system, a tablet configured to use the Android operating system, a smart watch configured to use the Android operating system, an Apple iPhone, an Apple iPad, or an Apple iWatch.

6. The smartphone interface device for phototherapy of claim 1, wherein one of a USB for a smartphone configured to use an Android operating system, a USB for a smart watch configured to use the Android operating system, a USB for an Apple iPhone, or a USB for an Apple iWatch is the smartphone connector.

7. The smartphone interface device for phototherapy of claim 1, wherein the light beam irradiating electrode is included in any one of an arthritis treatment device, a pain treatment device, an angina treatment device, a stroke treatment device, an Alzheimer's treatment device, an apoplexy treatment device, a migraine treatment device, an edema treatment device, a gastric ulcer treatment device, a rhinitis treatment device, an asthma treatment device, an infertility treatment device, a urinary incontinence treatment device, a prostate treatment device, a menstrual pain treatment device, or a depression treatment device.

8. A smartphone interface device for phototherapy, the smartphone interface device for phototherapy having one side configured to be connected to a light beam irradiating electrode and another side configured to be connected to a smartphone, the smartphone interface device being further configured to receive a light beam irradiating electrode control command generated by an application program installed in the smartphone, and to control driving of the light beam irradiating electrode, the smartphone interface device for phototherapy further comprising:
    a main body having an MCU embedded therein, the MCU being configured to receive a light beam irradiating electrode control command related to a light beam irradiation intensity, a light beam irradiation time, a light beam irradiation pattern, and starting and ending of light beam irradiation from the smartphone, and to generate a light source driving control signal according to the received light beam irradiating electrode control command;
    a connecting cable connected to one side of the main body and configured to connect a smartphone connector;
    a light beam irradiating electrode connector connected to another side of the main body and configured to connect the light beam irradiating electrode;
    a USB OTG module embedded in the main body, connected to the smartphone connector and the MCU, and configured to perform communication between the smartphone and the MCU with the smartphone as a host;
    a voltage regulator embedded in the main body and configured to convert a voltage output from the smartphone into an operating voltage of the MCU; and
    a light beam irradiation driving part embedded in the main body and configured to receive the light source driving control signal from the MCU and to drive a light source according to the light source driving control signal received from the MCU.

9. The smartphone interface device for phototherapy of claim 8, further comprising an LED operation indicator light disposed at an upper surface of the main body and configured to indicate that the light beam irradiation driving part is driven and light is radiated from the light source.

10. The smartphone interface device for phototherapy of claim 8, wherein the smartphone is one of a smartphone configured to use an Android operating system, a tablet configured to use the Android operating system, a smart watch configured to use an the Android operating system, an Apple iPhone, an Apple iPad, or an Apple iWatch.

11. The smartphone interface device for phototherapy of claim 8, wherein one of a USB for a smartphone configured to use an Android operating system, a USB for a smart watch configured to use an the Android operating system, a USB for an Apple iPhone, or a USB for an Apple iWatch is the smartphone connector.

12. The smartphone interface device for phototherapy of claim 8, wherein one of an audio terminal or a micro USB is the light beam irradiating electrode connector.

13. The smartphone interface device for phototherapy of claim 8, wherein the light beam irradiating electrode is included in any one of an arthritis treatment device, a pain treatment device, an angina treatment device, a stroke treatment device, an Alzheimer's treatment device, an apoplexy treatment device, a migraine treatment device, an edema treatment device, a gastric ulcer treatment device, a rhinitis treatment device, an asthma treatment device, an infertility treatment device, a urinary incontinence treatment device, a prostate treatment device, a menstrual pain treatment device, or a depression treatment device.

* * * * *